(12) United States Patent
Geheb et al.

(10) Patent No.: US 9,381,373 B2
(45) Date of Patent: Jul. 5, 2016

(54) PROVIDING LIFE SUPPORT

(71) Applicant: ZOLL MEDICAL CORPORATION, Chelmsford, MA (US)

(72) Inventors: Frederick J. Geheb, Danvers, MA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 14/150,163

(22) Filed: Jan. 8, 2014

(65) Prior Publication Data

US 2014/0121717 A1    May 1, 2014

Related U.S. Application Data

(63) Continuation of application No. 13/538,470, filed on Jun. 29, 2012, now Pat. No. 8,639,348.

(51) Int. Cl.
*A61N 1/39* (2006.01)
*A61N 1/362* (2006.01)

(52) U.S. Cl.
CPC ............. *A61N 1/3987* (2013.01); *A61N 1/3625* (2013.01); *A61N 1/39* (2013.01); *A61N 1/3937* (2013.01)

(58) Field of Classification Search
CPC ..... A61N 1/39; A61N 1/3925; A61N 1/3993; A61N 1/372–1/37288
USPC ..................................... 607/6, 60, 32; 128/93
See application file for complete search history.

(56) References Cited

U.S. PATENT DOCUMENTS

| | | | |
|---|---|---|---|
| 6,141,584 A | 10/2000 | Rockwell et al. | |
| 6,148,233 A | 11/2000 | Owen et al. | |
| 6,356,785 B1 | 3/2002 | Snyder et al. | |
| 6,405,083 B1 | 6/2002 | Rockwell et al. | |
| 6,438,417 B1* | 8/2002 | Rockwell et al. | .................. 607/5 |
| 6,597,948 B1 | 7/2003 | Rockwell et al. | |
| 6,920,354 B2 | 7/2005 | Daynes et al. | |
| 7,231,258 B2* | 6/2007 | Moore et al. | ..................... 607/60 |
| 7,769,465 B2 | 8/2010 | Matos | |
| 2001/0047140 A1 | 11/2001 | Freeman | |
| 2003/0158593 A1* | 8/2003 | Heilman | ................. A61N 1/046 607/149 |
| 2004/0133242 A1 | 7/2004 | Chapman | |
| 2004/0143298 A1 | 7/2004 | Nova et al. | |
| 2006/0173498 A1* | 8/2006 | Banville | .................... A61N 1/39 607/5 |
| 2007/0233199 A1 | 10/2007 | Moore et al. | |

(Continued)

OTHER PUBLICATIONS

Notification of Transmittal of the International Search Report and the Written Opinion of the International Searching Authority from corresponding PCT/US2013/047617 mailed Nov. 12, 2013.

(Continued)

*Primary Examiner* — Carl H Layno
*Assistant Examiner* — Erin M Piateski
(74) *Attorney, Agent, or Firm* — Fish & Richardson P.C.

(57) ABSTRACT

Systems and methods of providing life support are provided. A life support system includes a first life support device that has a control unit and is configured to apply a life support protocol to a subject. The first life support device also includes a memory unit that can store life support protocol information, and the control unit can provide the life support protocol information to a second life support device. The control unit can also receive operating instructions from the second life support device based on the life support protocol information, and can implement the operating instructions.

19 Claims, 4 Drawing Sheets

(56) References Cited

U.S. PATENT DOCUMENTS

| | | |
|---|---|---|
| 2007/0299473 A1 | 12/2007 | Matos |
| 2008/0004663 A1 | 1/2008 | Jorgenson |
| 2008/0114406 A1* | 5/2008 | Hampton et al. ................ 607/3 |
| 2009/0005827 A1* | 1/2009 | Weintraub et al. ................ 607/6 |
| 2010/0268304 A1* | 10/2010 | Matos ................ G06F 19/3418 607/60 |
| 2010/0324612 A1 | 12/2010 | Matos |
| 2011/0288604 A1 | 11/2011 | Kaib et al. |
| 2012/0116272 A1* | 5/2012 | Hampton et al. ................ 601/21 |
| 2012/0146797 A1 | 6/2012 | Oskin et al. |
| 2014/0005736 A1 | 1/2014 | Geheb |

OTHER PUBLICATIONS

European Search Report, 13808725.9, Jan. 25, 2016, 7 pages.

\* cited by examiner

US 9,381,373 B2

PROVIDING LIFE SUPPORT

RELATED APPLICATIONS

This application claims the benefit under 35 U.S.C. §120 as a continuation of U.S. application Ser. No. 13/538,470, titled "PROVIDING LIFE SUPPORT," now U.S. Pat. No. 8,639,348, filed on Jun. 29, 2012, which is herein incorporated by reference in its entirety.

BACKGROUND

1. Technical Field

At least one embodiment of the present invention relates generally to systems and methods of providing life support.

2. Discussion of Related Art

Cardiac arrest and other health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival.

SUMMARY

Aspects and embodiments of the present invention are directed to systems and methods of providing life support. A first life support device is configured to monitor or apply treatment to a subject, such as a person. The first life support device obtains information about the monitoring or treatment of the subject, and provides this information to a second life support device. The first life support device receives operating instructions from the second life support device and implements the operating instructions.

At least one aspect is directed to a life support system. The life support system includes a first life support device that has a control unit and is configured to apply a life support protocol to a subject. The first life support device also includes a memory unit that can store life support protocol information, and the control unit can provide the life support protocol information to a second life support device. The control unit can also receive operating instructions from the second life support device based on the life support protocol information, and can implement the operating instructions.

In some embodiments, the first life support device includes at least one of an automated external defibrillator, a wearable therapeutic device, and a basic life support defibrillator, and the second life support device includes an advanced life support defibrillator. In an embodiment, the first life support device is configured to apply the treatment to the subject. The first life support device can also provide an indication of treatment capabilities of the first life support device to the second life support device.

In an embodiment, the operating instructions from the second life support device include an instruction to apply treatment to the subject from the second life support device. The second life support device can also display the operating instructions. In an embodiment, a monitor can display the operating instructions. In some embodiments, the control unit of the first life support device can provide life support protocol information that indicates at least one of a state of the first life support device and a treatment recommendation. The control unit can receive a prompt from the second life support device to provide the life support protocol information. In some embodiments, the second life support device can control the first life support device to apply treatment from the first life support device to the subject based on the operating instructions.

At least one aspect is directed to a method of providing life support. The method includes acts of applying a life support protocol from a first life support device to a subject, recording life support protocol information, and providing the life support protocol information to a second life support device. The method also includes acts of receiving operating instructions from the second life support device based on the life support protocol information, and implementing the operating instructions.

In some embodiments, the method includes acts of applying treatment to the subject from one of the first life support device and the second life support device, or implementing the operating instructions to couple the second life support device with the subject. The method can also include an act of displaying the operating instructions. Some embodiments include acts of indicating at least one of a state of the first life support device and a treatment recommendation, or acts of providing an indication of treatment capabilities of the first life support device to the second life support device. Some embodiments include acts of receiving a prompt to provide the life support protocol information or providing a prompt for the operating instructions.

In an embodiment, the method includes acts of providing instructions to decouple the first life support device from the subject, and providing instructions to couple the second life support device with the subject. Embodiments also include acts of receiving instructions to decouple the first life support device from the subject and receiving instructions to couple the second life support device with the subject.

At least one aspect is directed to a method of providing life support. The method includes an act of providing a first life support device configured to apply treatment to a subject, the first life support device configured to provide life support protocol information to a second device, receive operating instructions from the second device, and implement the operating instructions.

In accordance with another aspect, a method of providing life support using a first life support device is provided. The method comprises sending a first communication to the first life support device to alert the first life support device to a presence of a second life support device; receiving information from the first life support device concerning a life support protocol applied to a subject by the first life support device; and sending a second communication to the first life support device instructing the first life support device to modify the life support protocol applied to the subject by the first life support device based upon the information received from the first life support device.

In accordance with another aspect, a life support system is provided. The life support system comprises a first life support device having a control unit configured to receive information related to a life support protocol applied to a subject by a second life support device that is distinct from the first life support device. The first life support device is further configured to determine a second life support protocol to be applied to the subject, and to communicate operating instructions to the second life support device based upon the information to cause the second life support device to apply the second life support protocol to the subject.

These and other aspects and embodiments are discussed in detail below. The foregoing information and the following detailed description include illustrative examples of various aspects and embodiments, and provide an overview or framework for understanding the nature and character of the claimed aspects and embodiments. The drawings provide illustration and a further understanding of the various aspects and embodiments, and are incorporated in and constitute a part of this specification. The drawings, together with the remainder of the specification, serve to describe and explain the claimed aspects and embodiments.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
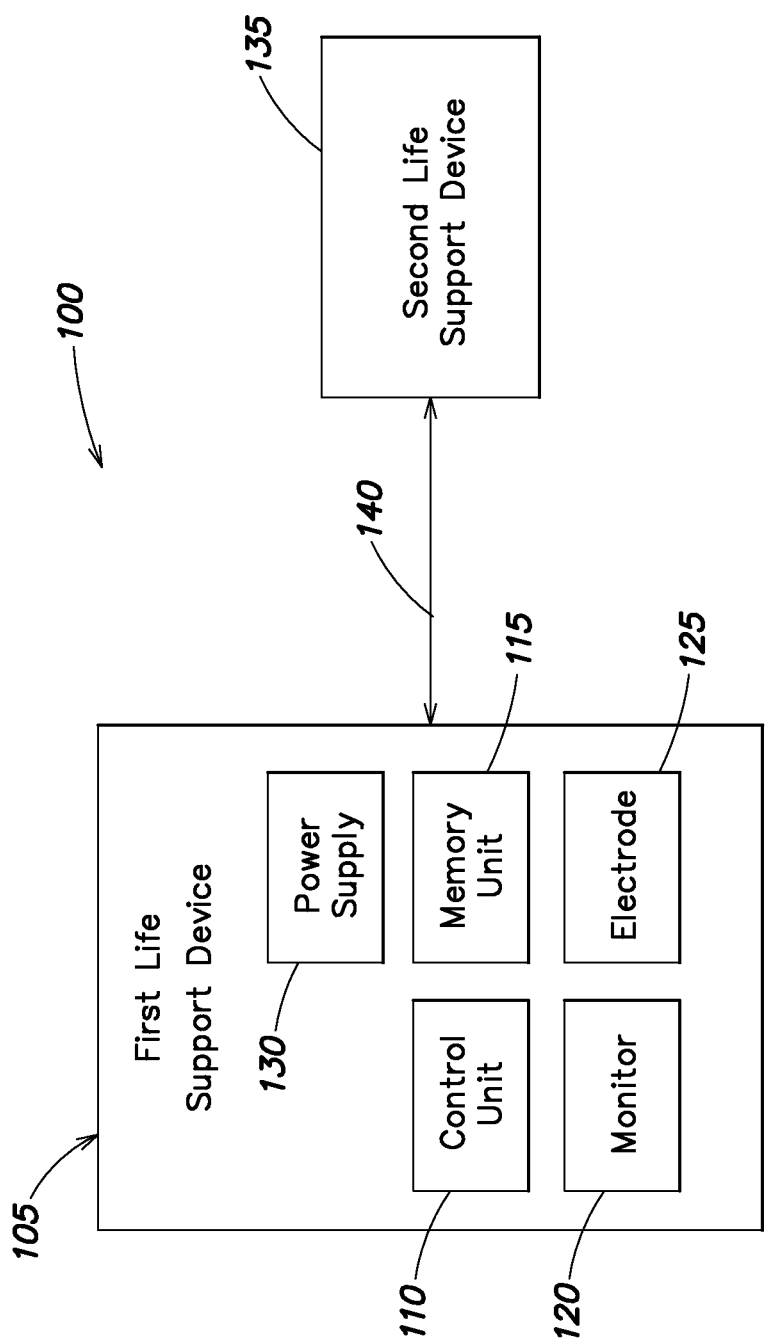
FIG. 1 is a block diagram depicting a life support system in accordance with an embodiment.

The systems and methods described herein are not limited in their application to the details of construction and the arrangement of components set forth in the description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein, is meant to encompass the items listed thereafter, equivalents thereof, and additional items.

Various aspects and embodiments are directed to a life support system. The life support system includes a first life support device that monitors or applies treatment to a subject. The first life support device can also record and communicate information concerning the monitoring or treatment to a second life support device. Based on this information, the first life support device receives operating instructions from the second life support device, and implements the received instructions, enhancing and providing a seamless integration or escalation of more advanced diagnosis, monitoring or treatment of the subject.

FIG. 1 is a block diagram of a life support system 100 in accordance with one embodiment. The life support system 100 includes at least one first life support device 105. In an embodiment, the first life support device 105 includes at least one Basic Life Support (BLS) device such as a BLS defibrillator or an Automated External Defibrillator (AED). In an embodiment, the first life support device 105 can be part of an external defibrillator or pacing device such as the AED Pro or AED Plus defibrillator, LifeVest®, ProPack M.D., X Series defibrillators, M Series defibrillators, R Series defibrillator BLS, or E Series defibrillator manufactured by the ZOLL Medical Corporation of Chelmsford Mass. In an embodiment, the first life support device 105 is specifically designed to be operated by a person with little or no medical training, and prompts the user with a series of instructions to treat a subject, and does not allow the user to deviate from the instructions. For example, the first life support device 105 can determine a power level of a defibrillation shock to be applied to the subject, and does not permit the user to adjust the power of the defibrillation shock. Rather, in this example, the user follows instructions to couple the first life support device 105 with the subject, for example by placing electrodes as instructed on the subject or by turning on the first life support device 105 and then the first life support device 105 automatically determines a treatment to be applied to the subject.

The first life support device 105 can include a pacing unit or a monitoring device that records health related information from a subject, such as information about the subject's respiration rate or heart activity. In an embodiment, the first life support device 105 includes an electrocardiograph that can display a subject's electrocardiogram (ECG). The first life support device 105 can be carried by paramedics, emergency health care providers, or first responders, such as police or firemen, or may be the type of life support device that is provided by a business or common carrier (e.g., an airline or bus) for use in an emergency situation. These or other users couple the first life support device 105 with a subject to monitor the subject to diagnose a condition (e.g., cardiac arrest, arrhythmia), or to apply treatment to the subject (e.g., defibrillation therapy, pacing therapy).

In an embodiment, the first life support device 105 includes at least one control unit 110. The control unit 110 controls operation of first life support device 105. For example, the control unit 110 can direct the first life support device 105 to monitor the medical status of a subject or apply treatment to the subject. The first life support device 105 can also include at least one memory unit 115. In an embodiment, the memory unit 115 is coupled to the control unit 110 and stores monitored information of the subject such as ECG information, or the subject's respiration rate. The memory unit 115 may also store historical information about the subject, information about the subject's age, weight, health, or gender, as well as information about past treatment applied by the life support device 105 to the subject. Such information may include the date and time at which treatment was applied to the subject, the nature of the treatment (e.g., the pulse width, amplitude, energy level of the treatment, whether monophasic or biphasic pulses were delivered, etc.)

The first life support device 105 can include at least one monitor 120. In an embodiment, the monitor 120 is coupled to the control unit 110 and the memory unit 115 and can display information about the subject such as the subject's ECG, heart rate, or respiration rate. The monitor 120 can also display other information about the subject (e.g., age, weight, etc.) as well as indicate what treatment has been applied to the subject and when that treatment was applied. In an embodiment, the monitor 120 indicates treatment is being applied to the subject during the application of that treatment by the first life support device 105. For example, the monitor 120 can display a warning that an electric shock is about to be applied or is being applied to the subject by first life support device 105. The warning can be visual or audio. In an embodiment, the monitor 120 includes a user interface where a user (e.g., the subject or a first responder) of the first life support device 105 can input information, such as information about the subject's health, appearance, age, weight, or gender. This information can be stored in the memory unit 115.

The first life support device 105 includes at least one electrode 125. In an embodiment, the at least one electrode 125 includes one or more sensing electrodes that monitor the subject and can detect ECG information, respiration information, or other information about the subject's condition. The at least one electrode 125 can alternatively include one or more therapy electrodes that can apply treatment to the subject, such as to administer pacing signals or a defibrillation shock. In some embodiments, the at least one electrode 125 can include both sensing electrodes and therapy electrodes as discrete electrodes, or combined into an integrated sensing/therapy electrode assembly. In an embodiment, the at least one electrode 125 is an external electrode that can be placed on a subject's body. In some embodiments, the at least one electrode 125 can be a subcutaneous or implantable electrode; a dry electrode, or an electrode to which a conductive fluid is applied to reduce impedance between the at least one electrode 125 and the subject.

In an embodiment, the first life support device 105 includes at least one power supply 130. The at least one power supply 130 may include batteries or other power supplies, including AC power supplies and uninterruptible power supplies. In an embodiment, the at least one power supply 130 provides power to the first life support device 105, including its components such as the control unit 110, the memory unit 115, the monitor 120, and the at least one electrode 125.

In an embodiment, the life support system 100 includes at least one second life support device 135. In an embodiment, the second life support device 135 includes at least one Advanced Life Support (ALS) device such as an ALS defibrillator. In an embodiment, the second life support device 135 is part of an external defibrillator or pacing device such as the M Series defibrillator, LifeVest®, ProPack M.D., X Series defibrillator, R Series ALS defibrillator, R Series Plus defibrillator, or E Series defibrillator manufactured by the ZOLL Medical Corporation of Chelmsford Mass. In an embodiment, the second life support device 135 is more advanced than first life support device 105 in that it may include functionality specifically adapted for use by a user with specialized medical training, such as an ALS provider, a doctor, or an emergency medical technician. For example, the second life support device 135 can be responsive to user input. A user can override treatment suggested by second life support device 135, or can modify a power level, pulse width, pulse type (e.g., monophasic or biphasic), or other parameter of the defibrillation shock to be applied to the subject. In this example, the user of the second life support device 135 can diagnose the subject and control second life support device 135 to monitor or treat the subject accordingly. Although not depicted in FIG. 1, the second life support device 135 generally includes at least one control unit, memory unit, monitor and electrode to monitor, diagnose, and apply treatment to a subject.

It should be appreciated that in a variety of circumstances a subject may become stricken and require medical attention. To attend to the stricken subject, the first life support device 105 is coupled to the subject and the control unit 110 applies a life support protocol. For example, the first life support device 105 can apply a life support protocol that includes monitoring the subject to determine if an event (e.g., cardiac arrest) that requires resuscitation or other treatment has occurred. In this example, the at least one electrode 125 can monitor the subject's heart activity and the monitor 120 can display the subject's ECG. The life support protocol can also include the application of treatment, such as a defibrillation or pacing treatment applied to the subject from the at least one electrode 125. The memory unit 115 can store the life support protocol information, such as ECG signals, or other information about heart activity, as well as treatment information, such as a history of treatment or monitoring life support protocols applied to the subject by the first life support device 105.

The control unit 110 of the first life support device 105 can communicate the life support protocol information to the second life support device 135. For example, a first responder can use the first life support device 105 to apply a life support protocol to treat or monitor a subject who is experiencing a cardiac arrest when another responder with a second life support device 135 arrives on scene, or when the subject arrives in a treatment facility where the second life support device 135 is present. In an embodiment, the second life support device 135 is more advanced than first life support device 105, and can monitor or apply treatment to the subject that is beyond the capabilities of first life support device 105.

In an embodiment, the control unit 110 of the first life support device 105 communicates information about the subject to the second life support device 135, and receives instructions from the second life support device 135 via at least one wired or wireless communication path 140. For example, communications path 140 may comprise any type interface or network such as a Universal Serial Bus (USB), local area network (LAN), Wireless LAN (WLAN), Patient Area Network (PAN) and/or Medical Body Area Network (MBAN). The first life support device 105 can implement these instructions while operatively coupled with the subject, and in an embodiment can operate under the control of the second life support device 135 that is in communication with first life support device 105 via communication path 140, but not physically coupled with the subject, (e.g., wirelessly). The second life support device 135 can include a controller to process information about the subject, including processing information monitored by first life support device 105, logistical information provided by first life support device 105, or treatment information indicative of treatment activity provided or being provided by first life support device 105 via communication path 140. Based on this information, the second life support device 135 can determine how to proceed, and can provide instructions to the first life support device 105 via communication path 140 to, for example, continue to monitor the subject, apply treatment to the subject, or to shut down and decouple from the subject so that the second life support device 135 can be coupled with the subject to monitor or apply treatment to the subject.

In accordance with one embodiment, the first life support device 105 may be capable of providing treatment to the subject in response to instructions received from the second life support device 135 that it would otherwise be unable to perform on its own. For example, the first life support device 105 may have a first or default mode of operation when used as a stand-alone device and a second or configurable mode of operation when appropriately instructed by another life support device, such as the more advanced second life support device 135. In the first mode of operation the first life support device 105 may be configured to monitor the subject and provide treatment to the subject in accordance with a pre-configured treatment protocol that cannot be altered or changed by the user (who is assumed to lack the requisite medical training). In the second mode of operation, the first life support device can be instructed to deviate from that pre-configured treatment protocol at the instruction of the second life support device (which is assumed to be operated under the control of a trained medical service provider). For example, where the first life support device 105 is an AED or a BLS defibrillator, the first life support device 105 may be instructed to vary the pulse width, amplitude, energy level or type of defibrillation pulses applied at the direction of the second life support device 135. Such dual mode operational capability may dispense with the time delay associated with shutting down and decoupling the first life support device 105 from the subject and then coupling the second life support device 135 to the subject.

Figure 2:
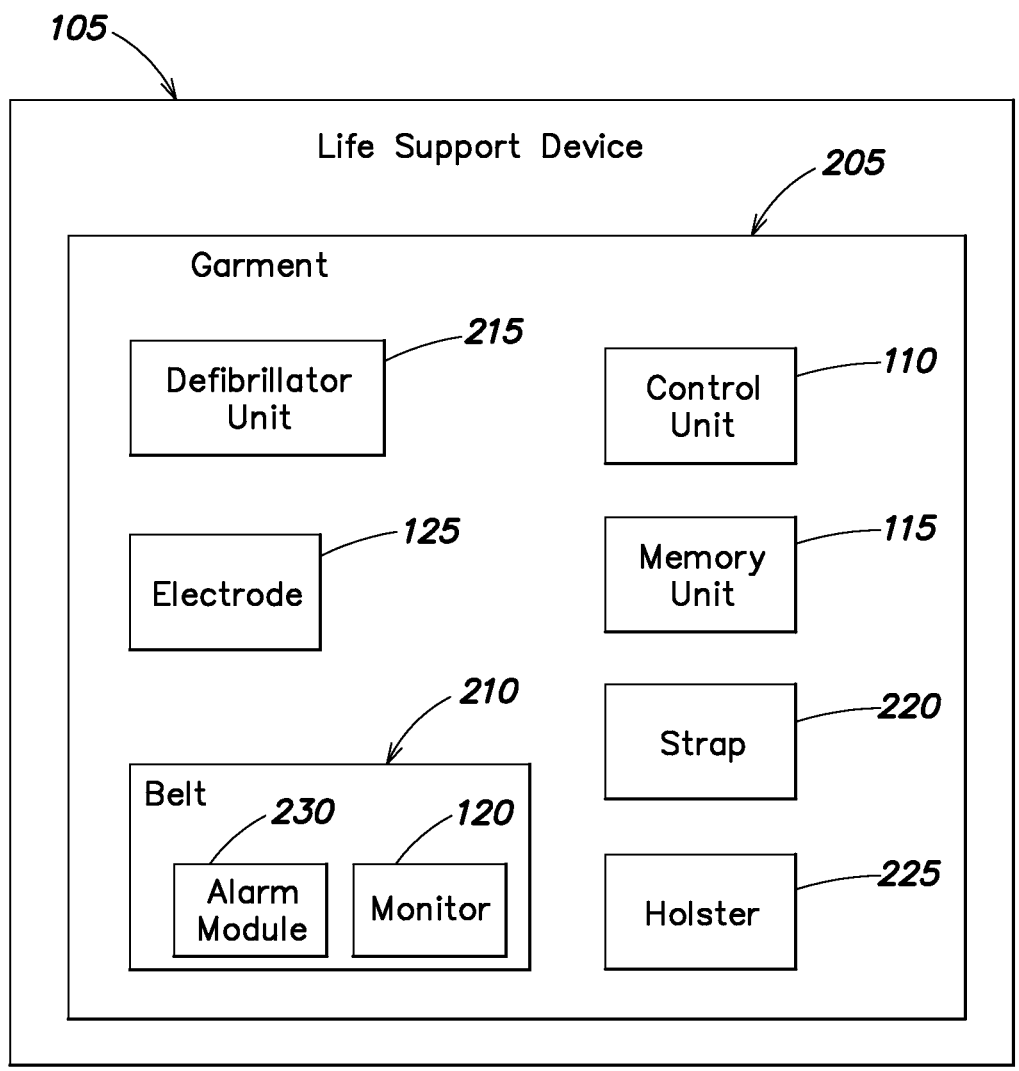
FIG. 2 is a block diagram depicting a life support device in accordance with an embodiment.

FIG. 2 is a block diagram in accordance with another embodiment in which the first life support device 105 is a wearable therapeutic or monitoring device associated with at least one garment 205. The garment 205 may have the shape of a vest or shirt. The garment 205 may also include at least one belt 210 worn about the subject's waist, at a higher location about the subject's chest, or at other locations between the subject's waist and shoulders. In an embodiment, clothes that are not part of the garment 205 may be present between the garment 205 and the subject, and at least parts of the first life support device 105 can be worn under or over the subject's clothes.

The first life support device 105 can be a wearable therapeutic device that includes at least one defibrillator unit 215. In an embodiment, the at least one defibrillator unit 215 is an external defibrillator housed in the garment 205. The at least one defibrillator unit 215 can also be part of a Basic Life Support system. Defibrillator unit 215 may include a power supply 130 or a separate power source. In an embodiment, defibrillator unit 215 is attached to belt 210, at least one shoulder strap 220, or is disposed in holster 225. In an embodiment, defibrillator unit 215 is electrically coupled with at least one electrode 125. The at least one electrode 125 may be disposed in or on the belt 210, the shoulder strap 220 or at other locations on the garment 205.

In an embodiment, control unit 110 monitors a subject's condition. For example, the at least one electrode 125 can include one or more ECG sensing electrodes that sense electrical activity of the subject's heart. When, for example, an arrhythmic event is detected, an alarm module 230 or the monitor 120 can provide a warning that the subject wearing the first life support device 105 is in danger of, or is experiencing cardiac arrest or other type of cardiac distress. The warning can be audio, visual, haptic, or combinations thereof. The memory unit 115 can store alarm information such as the nature, type, and cause of the alarm and the control unit 110 can provide this information to the second life support device 135 for further processing or analysis or for a determination, by the second life support device 135, of operating instructions such as further monitoring or treatment of the subject.

In an embodiment, the at least one electrode 125 is a permanent component of garment 205. For example, the at least one electrode 125 can be integral to the garment 205 and disposed proximate to the subject's chest, back, or abdomen when the subject is wearing the garment 205. In an embodiment, the at least one electrode 125 includes a plurality of therapy electrodes disposed proximate to the subject so that when defibrillator unit 215 delivers a defibrillation shock, a circuit is formed including at least a portion of the subject's body, defibrillator unit 215, and the therapy electrodes. Wires, conductive thread, or other conductive elements can be embedded in or attached to garment 205 to couple control unit 110, defibrillator unit 215, the at least one electrode 125, monitor 120 and alarm module 230.

Figure 3:
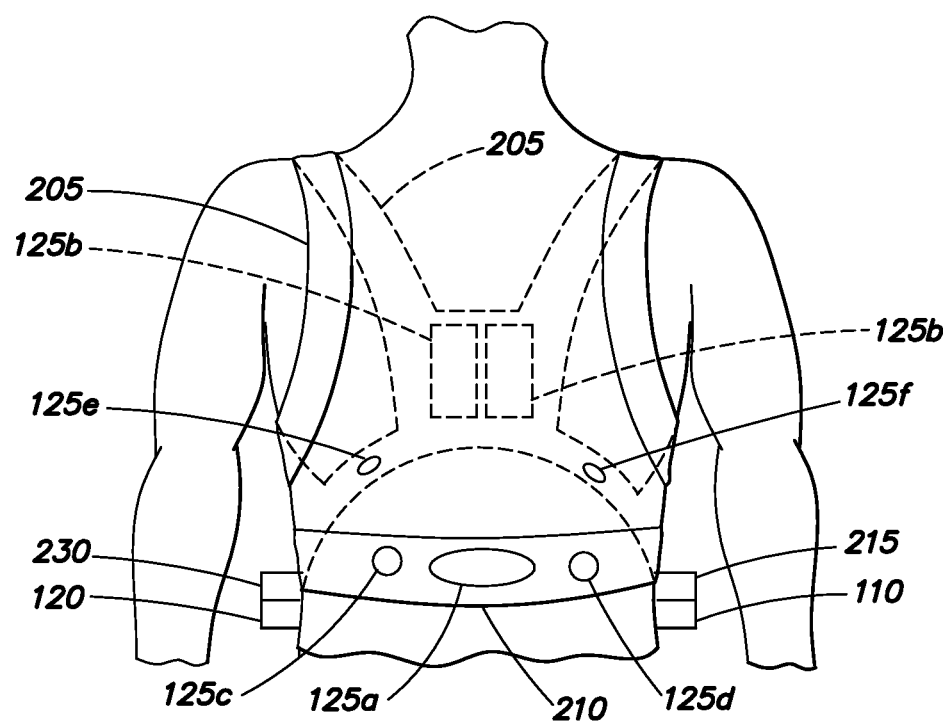
FIG. 3 is a schematic diagram depicting a life support device in accordance with another embodiment.

FIG. 3 is a schematic diagram depicting the first life support device 105 including the garment 205 in accordance with an embodiment. The garment 205 can include one front therapy electrode 125a and two rear therapy electrodes 125b. In an embodiment these therapy electrodes are configured to administer defibrillation and/or pacing therapy to the subject wearing the first life support device 105 and the first life support device 105 further includes a plurality of sensing electrodes 125c, 125d, 125e, and 125f configured to sense cardiac activity of the subject. The electrodes 125a-f can be disposed in anterior, posterior, or lateral positions on the subject, for example proximate to the subject's chest, back, or sides. In an embodiment, a first sensing electrode is disposed in an anterior position, and a second sensing electrode is disposed in a posterior position. In a further aspect of this embodiment, two sensing electrodes are disposed in opposing lateral positions. The garment 205 can include pockets or sleeves configured to house the sensing and/or therapy electrodes. Any of the control unit 110, the defibrillator unit 215, the monitor 120, and the alarm module 230 can be attached to the belt 210 of the garment 205. The control unit 110 may be part of the defibrillator unit 215. In an embodiment, the control unit 110 directs the operation of the defibrillator unit 215, the alarm module 230, and the monitor 120.

In an embodiment, the first life support device 105 may include the wearable therapeutic device described in commonly owned U.S. patent application Ser. No. 13/109,079, entitled "Wearable Therapeutic Device," filed on May 17, 2011, or U.S. patent application Ser. No. 13/315,894, entitled "Wearable Therapeutic Device," filed on Dec. 9, 2011, each of which is incorporated by reference herein in its entirety. The referenced applications generally describe a wearable therapeutic device, such as a LifeVest® wearable defibrillator available from ZOLL Medical Corporation of Chelmsford Mass.

The subject can be wearing the first life support device as illustrated in FIG. 3, or first responders, health care providers, or the subject himself can couple the first life support device 105 (FIG. 1) with the subject. The first life support device 105 can be coupled with the subject while the subject is experiencing a cardiac event or otherwise in need of immediate medical attention. In an embodiment, the subject wears the first life support device 105 substantially continuously for a period of time (e.g., while sleeping, working, exercising, or going about daily activities) in the absence of a cardiac event. The first life support device 105 can apply a life support protocol to the subject, for example by monitoring the subject's condition or by applying treatment to the subject.

In an embodiment, the first life support device 105 transmits information to the second life support device 135, for example via wired or wireless connections, including wired or wireless universal serial bus connections and short range Bluetooth® wireless connections between the first life support device 105 and the second life support device 135. It should be appreciated that other communication standards and protocols that are capable of communicating over longer distances may alternatively be used, such as TCP/IP, Ethernet, Wireless Ethernet, GSM, etc. The information provided can include life support protocol information carried out by the first life support device 105 as well as general information about the subject. In an embodiment, the first life support device 105 detects the presence of the second life support device 135, for example via an active, passive, or semi-passive radio frequency identification (RFID) communication system, and establishes a connection with and provides information to the second life support device 135 responsive to this detection. Alternatively, the second life support 135 may detect the presence of the first life support device 105 when brought in proximity with the first life support device. In an alternative embodiment, a rescuer or health care provider (e.g., doctor, nurse, or emergency medical technician) couples the first life support device 105 with the second life support device 135.

In an embodiment, the second life support device 135 determines a course of action to follow responsive to information received from the first life support device 105. Information received from the first life support device 105 may include the date and time of any defibrillation shocks applied to the subject, the pulse width, amplitude, and energy level of those treatments, ECG and/or other information (such as pulse oxygen level, blood pressure, tidal carbon dioxide measurements, etc.) before and after treatment, etc. For example, the second life support device 135 can determine that the first life support device 105 should continue monitoring or treating the subject, or should apply a new or different treatment to the subject, e.g., defibrillation or pacing. In an embodiment, the second life support device 135 determines that a level of treatment applied by the first life support device 105 should be modified, e.g., a stronger or weaker defibrillation shock based, for example, on monitored information of the subject's response to previous treatment, or based on the subject's weight or size. The first life support device 105 can also provide information about the operating status of the first life support device 105, such as remaining available power from the power supply 130, or the time necessary before the first life support device 105 is scheduled or able to apply defibrillation therapy to the subject.

In an embodiment, the second life support device 135 determines the capabilities of the first life support device 105. For example, the first life support device 105 can provide information about its monitoring and treatment capabilities to the second life support device 135. In an embodiment, this information may be provided as a list of features or operational capabilities supported by the first life support device 105. Alternatively, this information may be provided as an identifier that identifies the model number and manufacturer of the first life support device 105. In this alternative embodiment, the second life support device 135 may include a look-up table, for example, stored in a memory of the second life support device, by which it can associate the features and operational capabilities supported by the first life support device, based upon the manufacturer and model number. In other embodiments, the second life support device may alternatively or additionally include a web interface by which it can identify the features and capabilities of the first life support device based upon the manufacturer and model number. The second life support device 135 can then determine a course of action based on the supported features and treatment capabilities of the first life support device 105. For example, the second life support device 135 can determine that the first life support device 105 should continue or adjust its monitoring or treatment of the subject, or should decouple from the subject because no further monitoring or treatment is necessary, or because the first life support device 105 is not capable of providing the necessary treatment or monitoring. In an embodiment, the first life support device 105 receives a command from the second life support device 135 to stop applying a life support protocol to the subject so that the second life support device 135 may apply a new, different, or more advanced life support protocol that the first life support device 105 cannot implement.

A controller of the second life support device 135 can establish a master/slave relationship with the control unit 110 of the first life support device 105 where the second life support device 135 provides the control unit 110 with operating instructions that the control unit 110 executes. As noted previously, the operating instructions provided by the second life support device 135 may permit the first life support device 105 to perform treatment protocols that it would not be permitted to be performed when operated as a stand-alone device. In an embodiment, a power source of the second life support device 135 provides power to components of the first life support device 105, such as the monitor 120, the alarm module 230, or the electrodes 125 for monitoring or therapy treatment.

Figure 4:
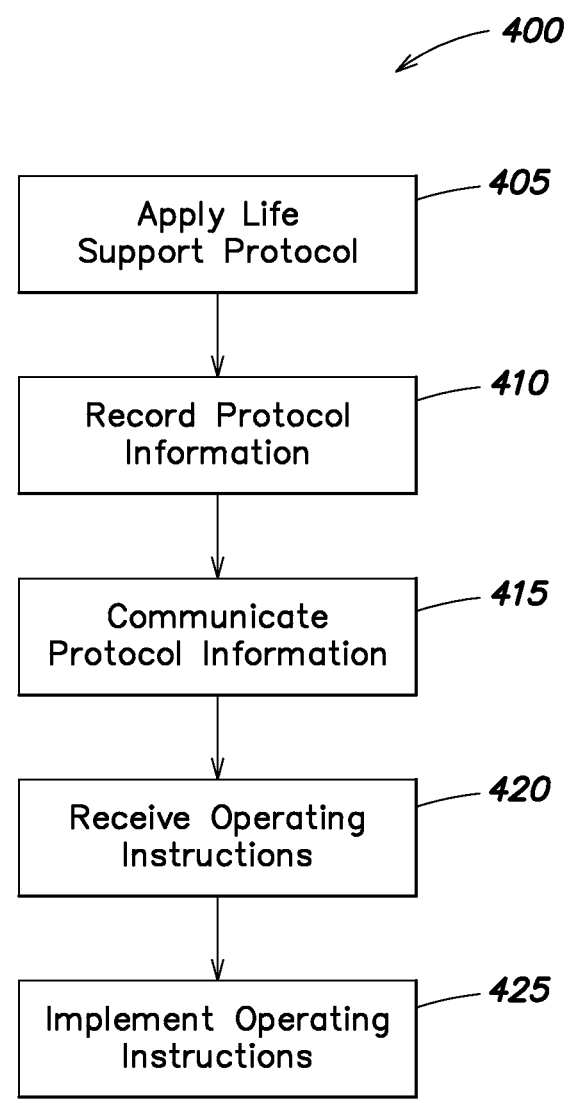
FIG. 4 is a flow chart depicting a method of providing life support in accordance with an embodiment.

FIG. 4 is a flow chart depicting a method 400 of providing life support in accordance with an embodiment. The method 400 includes an act of applying a life support protocol (ACT 405) by a first life support device. For example, applying a life support protocol can include one or more of monitoring a subject (e.g., monitoring cardiac or respiratory functions), applying treatment to the subject, or treating cardiac or respiratory conditions with defibrillation or pacing therapy, administering medicine, providing instructions to the subject or a health care provider present with the subject, or sounding an alarm, or transmitting a communication to alert a rescuer that the subject is in distress and requires assistance.

In an embodiment, method 400 includes an act of recording life support protocol information (ACT 410) by the first life support device. For example, a life support device can include a memory unit to store information about the life support protocol. The information can include data about the type of treatment (e.g., defibrillation, pacing) and the subject's response to treatment in the form of an ECG, for example. The information can also include information about the subject, such as an estimated weight provided by the subject or by an operator of the life support device. The information can also include monitored information about one or more of the subject's cardiac or respiratory activity before, during, or after any treatment or any symptoms of a medical condition. In an embodiment, recording protocol information additionally includes recording information that identifies an operating state of at least one life support device, whether electrodes are in sufficient contact with the subject to monitor or deliver therapy with the subject, or whether the power supply is sufficiently charged to administer defibrillation therapy.

Method 400 also includes an act of communicating the life support protocol information (ACT 415). In an embodiment, communicating the life support protocol information (ACT 415) includes transmitting monitoring or treatment information from the first life support device to a second life support device that receives the transmitted information. The information can be communicated wirelessly or via a wire communication path between the first and second life support devices. Communicating the life support protocol information (ACT 415) can include providing the subject's ECG, other cardiac or respiratory information to the second life support device. In an embodiment, communicating life support protocol information (ACT 415) includes providing information about the first life support device, such as its battery life or its monitoring or treatment capabilities, or identifying information of the first life support device, such as a model number. The second life support device can receive and analyze the model number to identify monitoring or treatment capabilities of the first device, based on its model number. Communicating life support protocol information (ACT 415) can also include providing information about treatment provided to the subject. The life support protocol information can be communicated (ACT 415) from the first life support device to the second life support device responsive to a prompt received by the first life support device, or responsive to detection of the second life support device by the first life support device. In an embodiment, the life support protocol information includes at least one treatment recommendation based, for example, on past treatment or monitored information. In an embodiment, communicating the life support protocol information (ACT 415) includes providing an indication of the monitoring or treatment capabilities of at least one life support device.

Method 400 further includes an act of receiving operating instructions (ACT 420) provided by the second life support device. The operating instructions can be received by the first life support device. In an embodiment, receiving operating instructions (ACT 420) occurs responsive to an act of communicating protocol information (ACT 415) from one life support device to another. For example, a first life support device can communicate information (ACT 415) to a second life support device and can receive operating instructions (ACT 420) based on the communicated information. The operating instructions can include instructions to monitor, treat, or decouple the first life support device from the subject. The received operating instructions can include a prompt for further information. In an embodiment, receiving operating instructions (ACT 420) includes receiving information via wired or wireless transmission from a life support device. Operating instructions can also be received (ACT 420) from a user via a user interface that is part of or connected to the first or second life support device. In an embodiment, receiving operating instructions (ACT 420) includes receiving instructions to couple the first or second life support device with a subject, for example for monitoring or treatment purposes.

The method 400 further includes an act of implementing operating instructions (ACT 425). Implementing operating instructions (ACT 425) can include executing instructions to monitor or treat a subject. Operating instructions can be implemented (ACT 425) by the first or second life support device. In an embodiment, implementing operating instructions (ACT 425) includes acts of implementing instructions to decouple the first life support device with a subject, or to couple the second life support device with the subject. Implementing operating instructions (ACT 425) can also include acts of receiving instructions from the second life support device to decouple the first life support device from the subject, receiving instructions from the second life support device to couple the second life support device with the subject, or receiving instructions to modify or adjust a treatment or monitoring protocol provided by the first life support device.

Having now described some illustrative embodiments, it is apparent that the foregoing is illustrative and not limiting, having been presented by way of example. In particular, although many of the examples presented herein involve specific combinations of method acts or system elements, those acts and those elements may be combined in other ways. Acts, elements and features discussed only in connection with one embodiment are not intended to be excluded from a similar role in other embodiments.

Note that in FIGS. 1 through 4, the enumerated items are shown as individual elements. In actual implementations of the systems and methods described herein, however, they may be inseparable components of other electronic devices such as a digital computer. Thus, actions described above may be implemented at least in part in software that may be embodied in an article of manufacture that includes a program storage medium. The program storage medium includes non-transitory and other data signals embodied in one or more of a carrier wave, a computer disk (magnetic, or optical (e.g., CD or DVD, or both)), non-volatile memory, tape, a system memory, and a computer hard drive.

Any references to embodiments or elements or acts of the systems and methods herein referred to in the singular may also embrace embodiments including a plurality of these elements. References to any act or element being based on any information, act or element may include embodiments where the act or element is based at least in part on the referenced information, act, or element.

References to "or" should be construed as inclusive so that any terms described using "or" may indicate any of a single, more than one, and all of the described terms.

The systems and methods described herein may be embodied in other specific forms without departing from the characteristics thereof. For example the nomenclature of first and second life support devices is for convenience of description. In some embodiments, the first and second life support devices are interchangeable; the first life support device can include components and characteristics described with reference to the second life support device, and the second life support device can include components and characteristics described with reference to the first life support device. The first and second life support devices can have redundant or overlapping monitoring or treatment capabilities. In an embodiment, the second life support device is a tablet computer, smart phone, or personal digital assistant capable of communicating with the first life support device. The foregoing embodiments are illustrative rather than limiting of the described systems and methods.

What is claimed is:

1. A life support system comprising:
a first life support device having a first mode of operation in which the first life support device is operated as a stand-alone device to deliver a first life support protocol to a subject under control of a control unit of the first life support device, the first life support device being configured to provide information about its treatment capabilities to a second life support device that is distinct from the first life support device, the first life support device having a second mode of operation in which the first life support device is configured to receive operating instructions from the second life support device and deliver to the subject, under control of the control unit of the first life support device and based on the operating instructions, a life support protocol that the first life support device is incapable of performing when operated as a stand-alone device, wherein the operating instructions are based upon the provided information about the treatment capabilities of the first life support device.

2. The life support system of claim 1, wherein the first life support device is configured to record information regarding one of the subject and the first life support protocol and to communicate the information to the second life support device.

3. The life support system of claim 2, wherein the first life support device is configured to wirelessly detect a presence of the second life support device, and to communicate the information to the second life support device responsive to detection of the presence of the second life support device.

4. The life support system of claim 2, wherein the operating instructions are determined by the second life support device in response to an analysis, performed by the second life support device, of the information regarding one of the subject and the first life support protocol.

5. The life support system of claim 1, wherein the first life support protocol is automatically determined by the first life support device and parameters of the first life support protocol are not adjustable by a user when the first life support device is operated in the first mode of operation.

6. The life support system of claim 5, wherein parameters of the first life support protocol are adjustable by the user when the first life support device is operated in the second mode of operation.

7. The life support system of claim 1, including at least one therapy electrode configured to administer the first life support protocol to the subject.

8. The life support system of claim 1, wherein the first life support device is a wearable device associated with at least one garment configured to be worn by the subject on the chest of the subject, the garment including at least one belt and at least one shoulder strap.

9. The life support system of claim 1, wherein the first life support device includes a defibrillation unit and the first life support protocol includes defibrillation therapy.

10. The life support system of claim 1, wherein the first life support device is configured to communicate identification information of the first life support device to the second life support device.

11. The life support system of claim 1, wherein the first life support device is configured to provide treatment information indicative of treatment performed on the subject by the first life support device to the second life support device and the second life support device is configured to provide operating instructions to the first life support device based on the treatment information.

12. The life support system of claim 1, wherein the control unit is configured to determine the first life support protocol to be applied to treat the subject and a memory unit operatively coupled to the control unit and configured to store information concerning the first life support protocol, the control unit being configured to transmit the information concerning the first life support protocol to the second life support device, to receive operating instructions from the second life support device concerning a second life support protocol to be applied to treat the subject based upon the information concerning the first life support protocol, and to implement the operating instructions on the first life support device to treat the subject by applying the second life support protocol to treat the subject using the first life support device.

13. The life support system of claim 1, wherein the first life support device is configured to provide the information about its treatment capabilities to the second life support device by providing a model number of the first life support device to the second life support device, and the second life support device is configured to identify the information based on the model number.

14. The life support system of claim 1, wherein the first life support device is configured to prompt a user with one or more instructions for treating the subject with the first life support device under control of the control unit.

15. The life support device of claim 1, wherein each of the first life support device and the second life support device is independently capable of delivering electrical therapy to the subject.

16. The life support system of claim 1, wherein the second life support device is a portable electronic device selected from the group consisting of a tablet computer, a smart phone, and a personal digital assistant.

17. A life support system comprising:
a first cardiac defibrillator having a first mode of operation in which the first cardiac defibrillator is operated as a stand-alone device which delivers a first life support protocol to a subject under control of a control unit of the first cardiac defibrillator, the first cardiac defibrillator being configured to provide information about its treatment capabilities to a second cardiac defibrillator that is distinct from the first cardiac defibrillator, the first cardiac defibrillator having a second mode of operation in which the first cardiac defibrillator is configured to receive operating instructions from the second cardiac defibrillator and deliver to the subject, under control of the control unit of the first cardiac defibrillator and based on the operating instructions, treatment that the first cardiac defibrillator would otherwise be unable to perform on its own, wherein the operating instructions are based upon the provided information about the treatment capabilities of the first life support device, the treatment including applying a defibrillation pulse having an electrical characteristic that the first cardiac defibrillator is incapable of applying when operating as a stand-alone device.

18. The life support system of claim 17, wherein the electrical characteristic includes one or more of a pulse width, an amplitude, and an energy of the defibrillation pulse.

19. A life support system comprising:
a first life support device having a first mode of operation in which the first life support device is operated as a stand-alone device to deliver a first life support protocol to a subject under control of a control unit of the first life support device, the first life support device being configured to provide information about its monitoring and treatment capabilities to a second life support device that is distinct from the first life support device, the first life support device having a second mode of operation in which the first life support device is configured to receive operating instructions from the second life support device and deliver to the subject, under control of the control unit of the first life support device and based on the operating instructions, a life support protocol that the first life support device is incapable of performing when operated as a stand-alone device, wherein the operating instructions are based upon the provided information about the monitoring and treatment capabilities of the first life support device, each of the first life support device and the second life support device being independently capable of delivering electrical therapy, wherein the life support protocol delivered by the first life support device when operated in the second mode of operation includes application of a defibrillation pulse having an electrical characteristic that the first life support device is incapable of applying when operating as a stand-alone device.

* * * * *

UNITED STATES PATENT AND TRADEMARK OFFICE
CERTIFICATE OF CORRECTION

| | |
|---|---|
| PATENT NO. | : 9,381,373 B2 |
| APPLICATION NO. | : 14/150163 |
| DATED | : July 5, 2016 |
| INVENTOR(S) | : Frederick J. Geheb and Gary A. Freeman |

It is certified that error appears in the above-identified patent and that said Letters Patent is hereby corrected as shown below:

In the claims,

Column 13, Line 26, In Claim 12, delete "subj ect" and insert -- subject --, therefor.

Signed and Sealed this
Twenty-third Day of August, 2016

Michelle K. Lee
*Director of the United States Patent and Trademark Office*